(12) United States Patent
Raider

(10) Patent No.: US 6,573,083 B1
(45) Date of Patent: Jun. 3, 2003

(54) METHOD OF WEIGHT REDUCTION IN HUMAN BEINGS

(76) Inventor: Stanley Raider, 462 Hacienda Ave., Campbell, CA (US) 95008

( * ) Notice: Subject to any disclaimer, the term of this patent is extended or adjusted under 35 U.S.C. 154(b) by 81 days.

(21) Appl. No.: 09/645,221

(22) Filed: Aug. 24, 2000

(51) Int. Cl.$^7$ ................................................. C12N 1/20
(52) U.S. Cl. ............................. 435/252.33; 435/252.8; 514/892; 514/909
(58) Field of Search ........................... 424/78.01, 93.48, 424/93.2; 435/116; 514/909

(56) References Cited

U.S. PATENT DOCUMENTS

| | | |
|---|---|---|
| 5,084,565 A | 1/1992 | Parodos et al. |
| 5,744,331 A | 4/1998 | Nakano et al. |

FOREIGN PATENT DOCUMENTS

DE          19625582 A1  *  6/1996

OTHER PUBLICATIONS

Richardson, G.H., Standard Methods for the Examination of Dairy Products, 15th edition, American Public Health Services, pp. 54–67, 1985.*

Berkow, R. et al., "Enterobacteriaceae Infections", Marck Manual of Medical Information, Pocket Books, NY, pp. 950–954, 1997.*

Farges et al., Nutrition, 12 (3): 189–194, Supplementation of oral nutrition with pancreatic enzymes improves the nutritional status of aged endotoxemic rats, 1995.*

Lester Brown, Brian Halweil and Gary Gardner; World Watch News Release, dated Mar. 4, 2000; "Chronic Hunger and Obesity Epidemic Eroding Global Progress". –http://www.worldwatch.org/alerts/00304.html.

Brown, John C., Prof. at U. of Kansas; "What the Heck is an *E. coli*"; http://falcon.cc.ukans.edu/~brown/bugs.html.

Kirby, Jane, R.D.; "Dieting for Dummies"; Published by FDG Books Worldwide, Foster City, Ca. 94404.

Tovar, Kenneth, Prof. U. of Wisconsin at Madison; Description of His Course Bacteriology 330; http://www.bact.wisc.edu/bact330/bact330 homepage.

U.S. Food and Drug Administration; "Bad Bug Book"; Extract Tilted: "Enterotoxigenic *Escherichia coli*". http://vm.cfsan.fda.gov/~mow/.

Worldwatch News Release; "Chronic Hunger and Obesity Epidemic Eroding Global Progress", released on Mar. 4, 2000, http://www.worldwatch.org/alerts/00304.html.

J.D. Sleigh & M.C. Timbury; "Notes on Medical Bacteriology, 5$^{th}$ Ed.," 1998; pp 74 & 75; Churchill Livingstone, Edinburgh, Scotland.

M. Spraycar, Editor; "PDR Medical Dictionary, 1$^{st}$ Ed."; 1995; pp 476–943; Williams & Wilkins, Baltimore, Md, 21201 USA.

Author Unknown; "*E. coli* Serotypes"; web site:http://web.bham.ac.uk/bcm4ght6/path/sero.html; University of Birmingham, United Kingdom.

* cited by examiner

Primary Examiner—Christopher R. Tate
Assistant Examiner—Michele C. Flood

(57) ABSTRACT

A method of weight reduction in human beings, wherein a human ingests a laxative effective dosage of non-pathogenic *Escherichia coli* to produce a weight loss of up to two pounds within one week.

3 Claims, No Drawings

METHOD OF WEIGHT REDUCTION IN HUMAN BEINGS

BRIEF SUMMARY OF THE INVENTION

There are many different systems available to the individual seeking to lose weight. They run the gamut from ingesting drugs, both prescription and over-the-counter, to single component diets, i.e. 'low fat', 'high protein', 'low carbohydrate', with exercise. All of the foregoing regimens require some form of life-style change.

This invention, utilizing a bacteriological agent only, which is an integral part of the Gastro-Intestinal Tract, will create a measureable loss of weight in a given time period, i.e. up to two [2] pounds in one week.

A laxative effective dose of this bacteriological agent [Prototrophic E. coli] taken with a meal will cause an accelerated laxation within two [2] hours. This phenomenon will create the weight loss.

There does not have to be any changes in life-style for this invention to work.

DESCRIPTION

According to the Worldwatch News Report, dated Mar. 4, 2000, there are as many people on this planet that are considered overweight and/or obese, as there are people who suffer from malnutrition. "For the first time in human history, the number of overweight people rivals the number of underweight people, according to a new report from the Worldwatch Institute, a Washington, D.C. based research organization. While the world's underfed population has declined slightly since 1980 to 1.1 billion, the number of overweight people has surged to 1.1 billion."

In the United States, 55 percent of adults are overweight by international standards. A whopping 23 percent of American adults are considered obese.

Professor Kenneth Todar of the University of Wisconsin at Madison, Department of Bacteriology described a lecture of his course Bacteriology 330 with the following: "The GI tract of most warm-blooded animals is colonized by E. coli within a few hours or days after birth by the bacterium ingested in foods or water or directly from other individuals. The human bowel is usually colonized within 40 hours of birth. E.coli can adhere to the mucus overlying the large intestine. Once established, an E.coli strain may persist for months or years. Resident strains shift over a long period [weeks to months], and more rapidly after enteric infection or antimicrobial chemotherapy that perturbs the normal flora. The basis for these shifts and the ecology of Escherichia coli in the intestine of humans are poorly understood despite the vast amount of information on almost every other aspect of the organism's existence. In fact, the entire DNA base sequence of the E.coli genome is known."

Professor Todar further states in his course resume: "E. coli is a consistent inhabitant of the human intestinal tract, and it is the PREDOMINANT FACULTATIVE ORGANISM IN THE HUMAN GI TRACT; however, it makes up a very small proportion of the total bacterial content. The number of anaerobic Bacteroides in the bowel outnumber E. coli by at least 20:1 The regular presence of E. coli in the human intestine and feces has led to the tracking of the bacterium in nature as an indicator of fecal pollution and water contamination."

Prof. Todar also states in his description of ENTEROTOXIGENIC E. coli: "ETEC[enterotoxic E. coli] are an important cause of diarrhea in infants and travelers in underdeveloped countries or regions of poor sanitation. The diseases vary from minor discomfort to a severe cholera-like syndrome."

Parodos, et al, in their U.S. Pat. No. 5,084,565, granted Jan. 28, 1992, state in the 'BACKGROUND OF THE INVENTION': "The term "Escherichia coli" as used herein, refers to bacteria classified in Bergey's Manual of Systemic Bacteriology[N. R. Krieg [ed.1, 1984, pp.408–423, Williams & Wilkins]. Detection of Escherichia coli [E. coli] is important in various medical and public health contexts. Escherichia coli [E. coli] was discovered to be ubiquitous in fecal material nearly a century ago. Thus, foods are tested for E.coli as the indicator organism for fecal contamination. Generally, the presence of E. coli in food and water is used as a measure of sanitary conditions. E. coli infection itself also can cause a variety of symptoms ranging from mild to severe gastroenteritis."

Parodos, et al, further state: "Pursuant to a standard laboratory method recommended by the FDA [FDA/BAM Bacteriological Analytical Manual, Chapters 5 and 6, 6th Edition, 1984, Supplement September 1987, Association of Analytical Chemists], the presence of E. coli has been traditionally detected by culturing an appropriately prepared sample on microbiological media under conditions favorable for growth of these organisms."

In his article, entitled 'What the Heck is an E. coli?', Prof. Brown describes and explains all the pitfalls and ramifications of Pathenogenic E. coli, particularly E. coli 0157:H7. In doing this, he also had to describe and explain Prototrophic E. coli, which I will quote out of context: "The presence of E. coli and other kinds of bacteria within our intestines is necessary for us to develop and operate properly, and for us to remain healthy—E. coli, along with other species of bacteria, provide us with many necessary vitamins, for example."

In reviewing the various materials written about Escherichia coli, Prof. Tovar, Parados, et. al. and Prof. Brown discuss pathogenic Eschericihia coli specifically, or in Parados' patent as a method of identifying Escherichia coli [non-specific]. Almost as an afterthought, they all mention/identify Prototrophic Escherichia coli [inactive E. coli] as one of the various different varieties of bacteria found in the Gastro-Intestinal tract of a healthy human being.

An excerpt from the U.S. Food and Drug Administration's book Bad Bug Book briefly describes Enterotxigenic Escherichia coli [ETEC]. As part of their description: "#3. Nature of the disease: Infective dose—Volunteer feeding studies indicate that a relatively large dose [100 million to 10 billion bacteria] of Enterotoxigenic E. coli is probably necessary to establish colonization of the small intestine . . . With high infective dose, diarrhea can be induced within 24 hours." Contrast this report with the core of this invention: am specifically calling for the use of Prototrophic Escherichia coli [inactive], which is one of several diverse bacteria that reside in the Gastro-Intestinal tract of healthy humans. Because Prototrophic E. coli reacts with the ingesta to digest, assimilate, help form vitamins, etc., and constitutes no more than 10% of the entire bacterial population. The addition of a small effective dose of Prototrophic E. coli will accelerate the time period to laxation and not diarrhea. It must be stressed that, because Prototrophic E. coli is already in the Gastro-Intestinal tract, all that is being done, is to change the quantity of Prototrophic E. coli to acieve the desired result: laxation in approximately 2 hours.

It must be stressed that one of the particular novelties of this invention is that no other foreign agent, i.e. chemical, pharmaceutical, herbal or other type of foodstuff is being introduced/ingested by the user. What is being ingested: a] is already residing in the Gastro-Intestinal Tract; and b] is being ingested only as an effective additional dose, so as to cause laxation only within two hours.

Food that is ingested at any meal requires approximately ten [10] hours to be completely assimilated by the body. If laxation occurs within two [2] hours, rather than the usual ten [10] hours, the body then loses approximately 75% of the ingested nutrients. The user continues with his/her daily routine, expending calories, but the net caloric intake is reduced by 75%, causing the body to utilize its own built-in fat reserves. This creates a small consistent, negative caloric intake, which, over time, causes a measurable weight loss.

The normal human intestine contains a given quantity of Prototrophic E. coli as an integral part of the digestive system. If this quantity is increased in a measured dose, laxation will occur within the given time period, [less than two [2] hours] as is proposed by the author of this invention. Care must be exercised, because larger quantities of Prototrophic E. coli can cause symptoms ranging from diarrhea to dehydration and in extreme cases, even death.

Because Prototrphic E. coli is an integral part [inhabitant] of the Gastro Intestinal Tract, its use is most beneficial in creating a proper balance for a 'time induced laxation'. The addition of a small quantity of Prototrophic E. coli, in effect, accellerates the peristoltic movement, with no other apparent side effect, but 'early' laxation, and its concommitant ultimate weight loss.

E. coli has been and is still used as a 'marker' for identifying contamination, whether water pollution or tainted foodstuffs. It is a symbiotic resident of the alimentary canal and is one of the many different components of ingested food digestion breakdown and assimilation. When its volume is increased drastically, E. coli and the other Enteric Bacteria can cause the following symptoms: cramps, high fever, diarrhea, bloody stool, etc., and in the instance of V. cholorae, dehydration and death.

PREFERRED EMBODIMENT

This invention utilizes the most simplistic method to cause a loss of weight in human beings over a given time period. The addition of an effective laxative dose of Prototrophic Escherichia coli with the ingestion of a meal, will cause the weight loss with the following caveats: a] Prototrophic E. coli is the singular only form of the bacteria from the family Enterobacteriacae to be used, all other varieties, including the other bacteria called Escherichia coli are pathogenic to some degree and are therefore, counter-indicated; b] the production of this product must be done under 'Clean Room' sterile conditions, thus avoiding other contaminants, which may cause gastritis and/or diarrhea; c] user must follow usage instructions implicitly because, doubling the dosage will not increase or double the weight loss. To the contrary, it will probably cause gastritis and/or severe diarrhea. Conversely, cutting the dosage in half to save money[?], will not produce the correct laxatious effect and therefore, not create a weight loss.

A further caveat, for which the author is aware, but has no other evidence, is that the human body itself, on whatever legitimate diet regimen, will not lose more than 2 to 3 pounds per week. This appears to be it's plateau.

It must also be noted that the particular bacterium referred to in this invention is, while small in quantity, up to 10% of the total bacterial volume, is a viable resident of the human Gastro-Intestinal tract. Its function is not fully understood, but it is helpful in peristalsis, the breakdown of nutrients, and absorption of nutrients and vitamins in the lower Gastro-Intestinal tract.

Also, the addition of Prototrophic E. coli [already residing in the Gastro-Intestinal tract] in correct dosage is much safer than introducing foreign substances to the Gastro-Intestinal tract.

It must be stressed that one of the particular novelties of this patent is that no other foreign agent, i.e. chemical, pharmaceutical, herbal or other type of foodstuff is being introduced/ingested by the user. What is being ingested: a] is already residing in the Gastro-Intestinal Tract; and b] is being ingested only as an effective additional dose, so as to cause laxation only within two hours.

Food that is ingested at any meal requires approximately ten [10] hours to be completely assimilated by the body. If laxation occurs within two [2] hours, rather than the usual ten[10] hours, the body then loses approximately 75% of the ingested nutrients. The user continues with his/her daily routine, expending calories, but the net caloric intake is reduced by 75%, causing the body to utilize its own built-in fat reserves. This creates a small consistent, negative caloric intake, which, over time, causes a measurable weight loss.

The normal human intestine contains a given quantity of Prototrophic E. coli as an integral part of the digestive system. If this quantity is increased in a measured dose, laxation will occur within the given time period, [less than two [2] hours] as is proposed by the author of this patent. Care must be exercised, because larger quantities of Prototrophic E. coli can cause symptoms ranging from diarrhea to dehydration and in extreme cases, even death.

Because Prototrophic E. coli is an integral part [inhabitant] of the Gastro Intestinal Tract, its use is most beneficial in creating a proper balance for a 'time induced laxation'. The addition of a small quantity of Prototrophic E. coli, in effect, accellerates the peristoltic movement, with no other apparent side effect, but 'early' laxation, and its concommitant ultimate weight loss. The suggested dosage should range from ten [10] million to not more than fifty [50] million Prototrophic E. coli bacteria, or its parts per million [ppm] equivalent.

E. coli has been and is still used as a 'marker' for identifying contamination, whether water pollution or tainted foodstuffs. It is a symbiotic resident of the alimentary canal and is one of the many different components of ingested food digestion breakdown and assimilation. When its volume is increased drastically, E. coli and the other Enteric Bacteria can cause the following symptoms: cramps, high fever, diarrhea, bloody stool, etc., and in the instance of V. cholorae, dehydration and death.

This invention utilizes Prototrophic E. coli, the non-pathogenic strain of E. coli, in a markedly reduced volume to cause laxation only, in a given time period [two hours], rather than the more drastic aforementioned symptoms.

Because of the difference between a 125 lb. woman seeking to lose between 5 and 10 lbs. and a 275 lb. man or woman who should lose 50+ lbs., the dosage ingested will vary up to ½ ml of liquid culture media.

Irrespective of who uses this invention, the dosage MUST be sufficient to cause laxation only, but not enough to cause gastroenteritis, diarrhea or any other debilitating side effect.

The author has been able to readily acquire culture samples of Prototrophic Escherichia coli from acknowledged Biological Supply Companies in the United States. These companies supply Prototrphic Escherichia coli only because either by company policy, governmental edict or both, they will not sell any variety of Pathogenic *Escherichia coli*; or for that matter any other pathogenic bacterium.

Replicating or culturing these samples is a matter of following standard bacteriological laboratory procedures. However, because of the nature of generic *Escherichia coli*, the author is concerned with the quality assurance/quality control of producing this product; a] Prototrophic *E. coli* only is to be cultured. It must be monitored over time because, there is the possibility of undesireable mutants being created. b] the dilution of the sample to parts per million must be adhered to both for colony count and contamination by other bacteria, molds, etc. c] dosages must be adhered to strictly, because double dosing will not create the desired end result, to the contrary, it will cause, at the very least, diarrhea or other debilitating reactions.

The other Enteric Bacteria are not considered by the author, because of the toxicity of these bacteria, at the present time. However, with additional research and development, they may be altered to become sufficiently tame as to be used to cause laxation ONLY with no other [negative] symptoms.

At no time, do Prof. Tovar, Parodos, et.al. or Prof. Brown mention or discuss the use of *E. coli* as a weight loss agent. Parenthetically, in a review of the literature relating to *E. coli*, no one else mentions this particular usage.

Microbiologists, who are working independantly worldwide, all of them, are doing research of one facet or another on Pathogenic *E. coli*. Not one of these Microbiologists is doing any research into Prototrophic *E. coli* [inactive *E. coli*].

This invention utilizes Prototrophic *E. coli*, the non-pathogenic strain of *E. coli*, in a markedly reduced volume to cause laxation only, in a given time period [two hours], rather than the more drastic aforementioned symptoms.

Because of the difference between a 125 lb. woman seeking to lose between 5 and 10 lbs. and a 275 lb. man or woman who should lose 50+ lbs., the dosage ingested will vary up to ½ ml of liquid culture media.

Irrespective of who uses this invention, the dosage MUST be sufficient to cause laxation only, but not enough to cause gastroenteritis, diarrhea or any other debilitating side effect.

The author has been able to readily acquire culture samples of Prototrophic *Escherichia coli* from acknowledged Biological Supply Companies in the United States. These companies supply Prototrphic *Escherichia coli* only, because either by company policy, governmental edict or both, they will not sell any variety of Pathogenic *Escherichia coli*; or for that matter any other pathogenic bacterium.

Replicating or culturing these samples is a matter of following standard bacteriological laboratory procedures. However, because of the nature of generic *Escherichia coli*, the author is concerned with the quality assurance/quality control of producing this product; a] Prototrophic *E. coli* only is to be cultured. It must be monitored over time because, there is the possibility of undesireable mutants being created. b] the dilution of the sample to parts per million must be adhered to both for colony count and contamination by other bacteria, molds, etc. c] dosages must be adhered to strictly, because double dosing will not create the desired end result, to the contrary, it will cause, at the very least, diarrhea or other debilitating reactions.

The other Enteric Bacteria are not considered by the author, because of the toxicity of these bacteria, at the present time. However, with additional research and development, they may be altered to become sufficiently tame as to be used to cause laxation ONLY with no other [negative] symptoms.

At no time, do Prof. Tovar, Parodos, et.al. or Prof. Brown mention or discuss the use of *E. coli* as a weight loss agent. Parenthetically, in a review of the literature relating to *E. coli*, no one else mentions this particular usage.

Microbiologists, who are working independently worldwide, all of them, are doing research of one facet or another on Pathogenic *E. coli*. Not one of these Microbiologists is doing any research into Prototrophic *E. coli* [inactive *E. coli*].

PRIOR ART

There are only two broad issues to be discussed as Prior Art: a] diet/weight loss regimens, and b] *Escherichia coli*.

Every diet regimen, almost by definition, requires that the user completely abandon his/her dietary intake, and adopt the new regimen's philosophy, i.e. High-protein, Low-carbohydrate; High-fibre, Low-calorie; Jennie Craig or Weight Watchers. Additionally, they all suggest [at a minimum], if not require a parallel exercise program to further enhance the weight loss.

Additionally, there are supplements that are: pharmaceuticals, over-the-counter medications and herbs which act as either appetite suppressants or stimulants.

Every one of these regimens and/or supplements have one singular factor in common with each other. That is: every regimen suggests or demands a change in the user's diet intake. Most also recommend a complete change in attitude toward eating.

The ingestion of an effective dose of Prototrphic *Escherichia coli* will cause laxation only, within two hours, and create a measureable weight loss of up to two [2] pounds per week, without any change in lifestyle or attitude. It is also not necessary to exercise to promote or enhance the weight loss, as the other diet regimens recommend.

I have cited Prof. Tovar, Dr. Brown, and Parodos, et.al. specifically because they all represent the different facets of the total research on *Escherichia coli*, which is the core of this patent. Prof. Tovar and Dr. Brown both dwell on Pathogenic *Escherichia coli*, while Parodos, et.al.'s patent refers to a method of identifying *Escherichia coli*.

All of the above, plus other researchers world-wide, refer to healthy or normal *Escherichia coli* [Prototrophic *Escherichia coli*] as an after-thought, stating simply: "it is a resident of the human Gastro-Intestinal tract, along with other bacteria, and it is useful in healthy digestion."

The author could not find any research on Prototrophic *Escherichia coli*, per se.

The ingestion of an effective dose of Prototrophic *Escherichia coli* will cause laxation only, within two hours, and create a measureable weight loss of up to two [2] pounds per week, without any change in lifestyle or attitude.

The aforementioned biologists and others world-wide, while studying *Escherichia coli*, have not made the bridge between Prototrophic *Escherichia coli* and weight loss.

What is claimed is:

1. A method of weight reduction in human beings, wherein a human being ingests a laxative effective dosage of a non-pathogenic strain of *Escherichia coli*, during a meal, so as to cause a premature laxation of the meal, and produce a weight loss of up to two pounds within one week.

2. The method described in claim 1, wherein the human being ingests the non-pathogenic strain of *Escherichia coli* by adding said bacteria to the meal.

3. The method described in claim 1, wherein the human being ingests the non-pathogenic strain of *Escherichia coli* immediately after the meal, but during the period the human being digests the meal.

* * * * *